(12) United States Patent
Neuser et al.

(10) Patent No.: US 8,977,022 B2
(45) Date of Patent: Mar. 10, 2015

(54) COMPUTED TOMOGRAPHY METHOD, AND SYSTEM

(75) Inventors: Eberhard Neuser, Wunstorf (DE); Alexander Suppes, Wunstorf (DE); Nils Rothe, Wunstorf (DE); Michael Hötter, Gehrden (DE); Anja Frost, Hannover (DE)

(73) Assignee: GE Sensing & Inspection Technologies GmbH, Hurth (DE)

( * ) Notice: Subject to any disclaimer, the term of this patent is extended or adjusted under 35 U.S.C. 154(b) by 137 days.

(21) Appl. No.: 13/808,925

(22) PCT Filed: Jul. 9, 2010

(86) PCT No.: PCT/EP2010/004191
§ 371 (c)(1),
(2), (4) Date: Feb. 4, 2013

(87) PCT Pub. No.: WO2012/003850
PCT Pub. Date: Jan. 12, 2012

(65) Prior Publication Data
US 2013/0163842 A1    Jun. 27, 2013

(51) Int. Cl.
*G06K 9/00*        (2006.01)
*G06F 19/00*        (2011.01)
*G06T 7/00*        (2006.01)

(52) U.S. Cl.
CPC ............ *G06F 19/321* (2013.01); *G06T 7/0012* (2013.01)
USPC ......................................................... 382/128

(58) Field of Classification Search
None
See application file for complete search history.

(56) References Cited

U.S. PATENT DOCUMENTS 6,510,241 B1 *   1/2003   Vaillant et al. ................ 382/154
6,862,233 B2    3/2005   Laurent
(Continued)

FOREIGN PATENT DOCUMENTS

JP    2000051204 A    2/2000
JP    2006525064 A    11/2006
(Continued)

OTHER PUBLICATIONS

Koichi, Ogawa, "Iterative Image Reconstruction in Emission Computed Tomography", Journal of Japanese Society of Radiological Technology, Jul. 2000, pp. 890-894, vol. No. 56, Issue No. 7.
(Continued)

*Primary Examiner* — Tahmina Ansari
(74) *Attorney, Agent, or Firm* — GE Global Patent Operation; Mark A. Conklin

(57) ABSTRACT

A computed tomography method for determining a volumetric representation of a sample comprising reconstruction initial volume data of the sample from x-ray projections of the sample taken by an x-ray system, determining a part of the reconstructed initial volume data to be updated, and executing an iterative update process configured to generate, using an iterative reconstruction method, updated volume data only for the part of the volume data determined to be updated. Determining the part of the sample volume to be updated comprises individually evaluating every single voxel in the reconstructed initial volume data, based on available quality information for the reconstructed initial volume data, whether or not the voxel fulfils a predetermined condition indicating that an update is required for the voxel, and the iterative update process generates the updated volume data only for the voxels which have been determined that an update is required.

12 Claims, 3 Drawing Sheets

(56) References Cited

U.S. PATENT DOCUMENTS

| | | |
|---|---|---|
| 6,862,335 B2 | 3/2005 | Basu |
| 7,394,927 B2 | 7/2008 | Proska et al. |
| 7,590,017 B2 | 9/2009 | Romanovskyy |
| 8,379,923 B2 * | 2/2013 | Ishikawa ................ 382/104 |
| 2004/0264625 A1 | 12/2004 | Basu |
| 2006/0269109 A1 | 11/2006 | Okada et al. |
| 2007/0098135 A1 | 5/2007 | Kunze |
| 2007/0297660 A1 * | 12/2007 | Hsieh et al. ............ 382/131 |
| 2008/0118020 A1 * | 5/2008 | Thibault et al. .......... 378/4 |
| 2010/0054394 A1 * | 3/2010 | Thibault et al. .......... 378/8 |
| 2013/0163842 A1 * | 6/2013 | Neuser et al. .......... 382/131 |

FOREIGN PATENT DOCUMENTS

| | | |
|---|---|---|
| JP | 2007117740 A | 5/2007 |
| JP | 2010127810 A | 6/2010 |
| WO | 2012003850 A1 | 1/2012 |

OTHER PUBLICATIONS

Unofficial English Translation of JP Office Action issued Mar. 11, 2014 in connection with corresponding JP Patent Application No. 2013-522107.

International Search Report from corresponding PCT Application No. PCT/EP2010/004191, Dated Oct. 19, 2010.

* cited by examiner

COMPUTED TOMOGRAPHY METHOD, AND SYSTEM

CROSS REFERENCE TO RELATED APPLICATIONS

This is a national stage application under 35 U.S.C. 0371(c) prior-filed, co-pending PCT patent application serial number PCT/EP2010/004191, filed on Jul. 9, 2010, the entire contents of which are incorporated herein by reference.

BACKGROUND OF THE INVENTION

Embodiments of the present invention relate to a computed tomography method, a computer program, a computing device and computed tomography system for determining a volumetric representation of a sample.

It is a general demand in computed tomography to reduce the influence of artefacts, to reduce the reconstruction time and to improve the quality of the reconstructed volume data.

Beyond this general demand, in many cases there exists the problem that certain regions of a given object cannot be scanned completely, or penetrated sufficiently, by x-rays during data acquisition, leading to regions of poor quality in the reconstructed volume data. Such cases relate for example to large objects which cannot be completely scanned in particular over the full 360°, like large flat components such as electronic boards; and/or materials which are hard to penetrate with x-rays, like lead in solder joints or inconel in turbine blades.

U.S. Pat. No. 6,862,335 B2 discloses a computed tomography method comprising an analytic reconstruction step for generating an initial reconstruction volume data, a volume partitioning step for separating the initial reconstruction volume into a good volume having a relatively good image quality and a poor volume having a relatively poor image quality, and an iterative reconstruction step for refining the reconstruction volume data in the poor volume. The volume partitioning step is based on geometrical considerations, namely the poor volume is defined by regions which are traversed by a relatively small number of radiation paths whereas the good volume is defined by regions which are traversed by a relatively large number of radiation paths, leading to a fixed and gross separation into good and poor volume parts for a given CT scanner geometry.

BRIEF SUMMARY OF THE INVENTION

Embodiments of the present invention provide a computed tomography method with reduced reconstruction time, where the volume data quality can be improved and/or the influence of artefacts can be reduced, particularly but not limited to cases where certain regions of the sample cannot be scanned with sufficient x-ray intensity or sufficiently sampled over 360° during data acquisition.

Embodiments of the present invention solve problems in the prior art. By individually evaluating for every single voxel in said volume data whether or not this voxel requires a further update, the volume which is to be updated can be tailored in a much more differentiated manner. In effect, the further update of exactly those voxels the quality of which is not yet sufficient can be achieved, leading to an increase in volume data quality, whereas the further update of those voxels the quality of which is already sufficient can be avoided, which leads to an reduced reconstruction time, in comparison to the gross volume partition of the prior art based on geometrical considerations.

Embodiments of the present invention is valuable in cases where certain regions of a given object cannot be scanned with sufficient x-ray intensity during data acquisition, and/or for objects which cannot be completely scanned over the full 360°, like large flat components such as large electronic boards or PCBA's, where satisfying solutions do not exist in the prior art. Other applications relate to materials which are hard to penetrate with x-rays, like lead in solder joints or large carbon fibre reinforced plastic plates, or inconel in turbine blades.

According to an embodiment, the evaluating step is performed in each iteration of the iterative update process, in particular prior to any further updated volume data generation. In this manner, the set of voxels to be updated can be dynamically adapted and their number can be reduced step by step from one update iteration to the next update iteration, leading to a further reduction of the overall reconstruction time.

According to an embodiment, the evaluating step comprises a step of generating an update mask comprising information about every single voxel for which a further update is required. The update mask can be stored in a memory and is used in the next update process iteration, which is a simple but fast and effective way of implementing the invention into a practical CT system.

According to an embodiment, the condition indicating that a further update is required for a particular voxel is whether the quality of this voxel falls below, or rises above, a predetermined threshold. However, the present invention is not restricted to this condition. Any other condition suited for indicating that an update is required for a particular voxel can be used.

According to an embodiment, individual confidence measures for every single voxel of the volume data, calculated after every reconstruction step for the reconstructed or updated voxels, are used as the quality information in the evaluation step. In an embodiment, the individual voxel confidence measures are determined essentially from process data of the reconstruction process, as described in particular in European patent application 09 01 4798.4 of the applicant which is incorporated herein by reference as a whole and in particular insofar as it concerns the calculation and properties of the individual voxel confidence measures. A confidence measure, or quality measure, of a particular voxel is a value unambiguously related to the probability that the density value of that voxel is correct. Alternatively the confidence measure may be related to the variance of the voxel density, the probability that the density value of that voxel is incorrect, an error in the voxel density, deviation to the true density, or the voxel accuracy. The confidence measure of a voxel gives quantitative information about the quality of the reconstructed voxel density. The entity of confidence measures over all voxels results in a confidence measure distribution, or confidence measure map, for the whole reconstructed sample volume. According to an embodiment, the confidence measures are determined essentially on the basis of the reconstructed volume data and/or the measured x-ray projections, only.

BRIEF DESCRIPTION OF THE DRAWINGS

In the following the present invention is described on the basis of embodiments with reference to the accompanying drawings, wherein.

DETAILED DESCRIPTION OF EXEMPLARY EMBODIMENTS OF THE INVENTION

Figure 1:
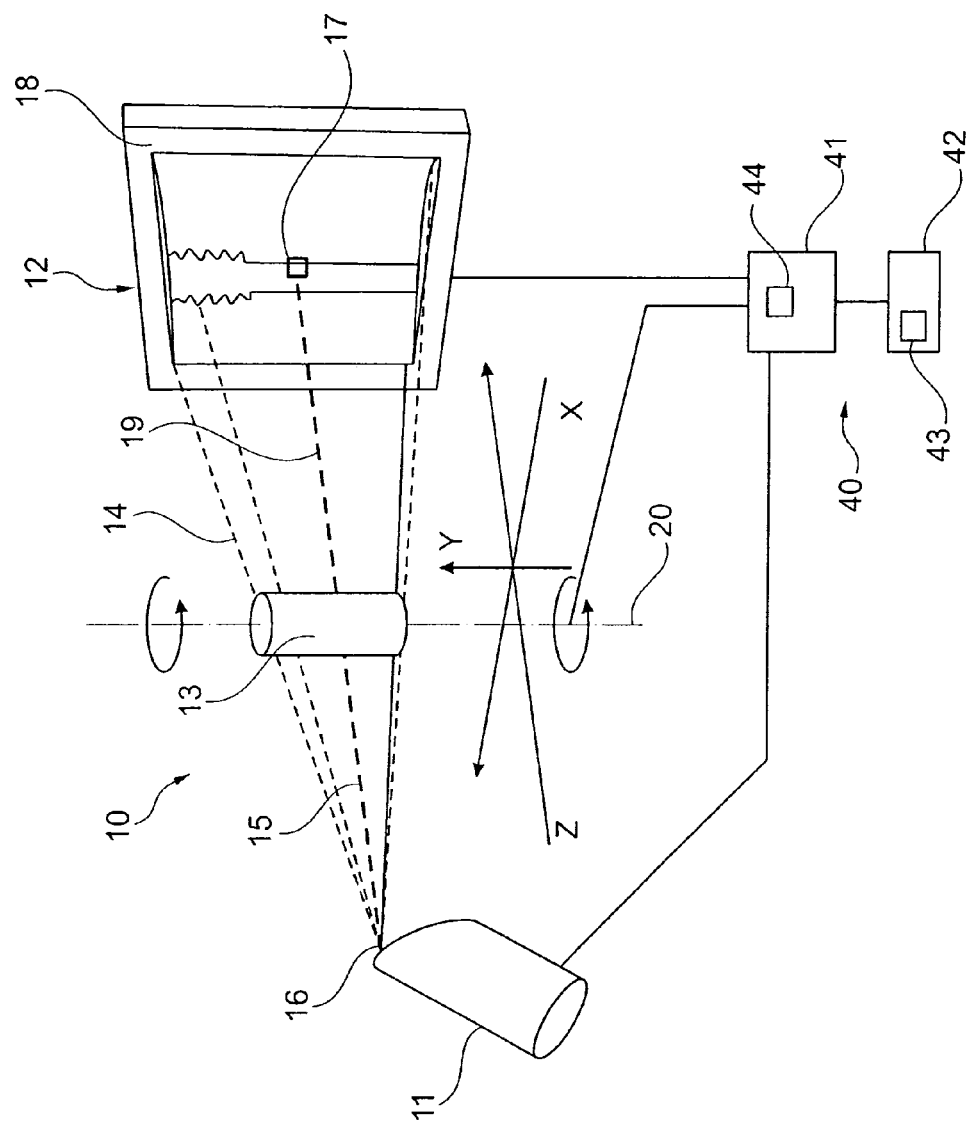
FIG. 1 is a schematic illustration of a computed tomography system according to an embodiment of the present invention.

The computed tomography system shown in FIG. 1 comprises an x-ray system 10 arranged to take a set of x-ray projections of a sample 13. Therefore, the x-ray system 10 comprises an x-ray source 11, in particular an x-ray tube, emitting an x-ray cone 14, an imaging device 12, in particular an x-ray detector, and a sample manipulator 20 which is adapted to rotate the sample 13 around a vertical axis. The x-ray detector 12 in the present example is a two-dimensional detector, however it is also conceivable to use a one-dimensional detector. A set of x-ray projections of the sample 13 are taken by step-wise rotating the manipulator around a predetermined small angular step and taking an x-ray projection at every rotation angle. The rotation is carried out over the full 360° if the dimensions of the sample allow this. However, in case of large objects, for example large electronic boards, the sample can be rotated only about a certain angular range less than 360°, and accordingly an incomplete data set of projections is taken using a less than 360° rotation of the sample 13. The CT system may in particular be a micro or nano CT system adapted to achieve a resolution below 10μm. However, the present invention is not restricted to such high-resolution CT systems.

An x-ray projection 18, an example of which is shown in FIG. 1, is a one- or two-dimensional image where the value of each pixel 17 represents the attenuation of the corresponding x-ray 15 from the focal spot 16 of the source 11 through the sample 13 resulting in a corresponding attenuated x-ray 19 to the pixel 17 under consideration. In general a set of x-ray projections 21 of a sample 13 is a plurality of x-ray projections 18 taken from different directions, which contains sufficient information to allow reconstruction of the volume structure of the full sample volume by a suited reconstruction technique.

The x-ray system 10 is not limited to rotating a sample manipulator 20 around a vertical axis. A set of x-ray projections may for example alternatively be obtained by rotating the x-ray system 10 around the fixed sample 13. In general the x-ray system 10 and the sample 13 are suitably movable relative to each other, which may include rotation about one or more vertical and/or horizontal axes for taking a set of x-ray projections. Alternative CT approaches like a tilted rotation axis (<90°) with respect to the beam axis and/or setups with a non constant magnification during taking a set of x-ray projections are possible.

The x-ray projections are read out from the imaging device 12 and sent to a computer apparatus 40 where they are stored in a memory 44 for subsequent evaluation and further processing. The computer apparatus 40 comprises a programmable computing device 41 in particular including a microprocessor or a programmable logic controller, and a user terminal 42 comprising a display device 43. The computing device 40 is programmed with a software for executing the computed tomography method which will be described in the following with reference to FIG. 2. Alternatively a separate computer unit may be used to evaluate the x-ray projections taken with the x-ray system 10.

In the embodiment shown in FIG. 1, the computing device 41 is arranged to control the x-ray system 10, in particular the x-ray source 11 and the sample manipulator 20 for taking the x-ray projections 18 of the sample 13. Alternatively a separate control unit may be used to control the x-ray system 10 for taking the x-ray projections 18 of the sample 13.

Figure 2:
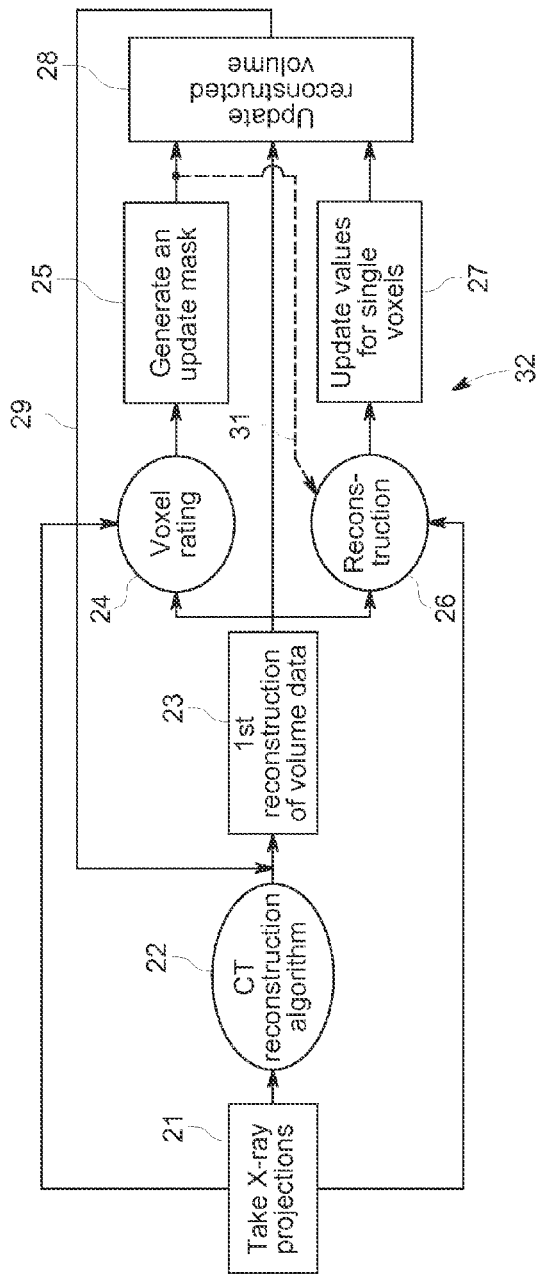
FIG. 2 is a flow diagram illustrating a computed tomography method according to an embodiment of the present invention.
Figure 2A:
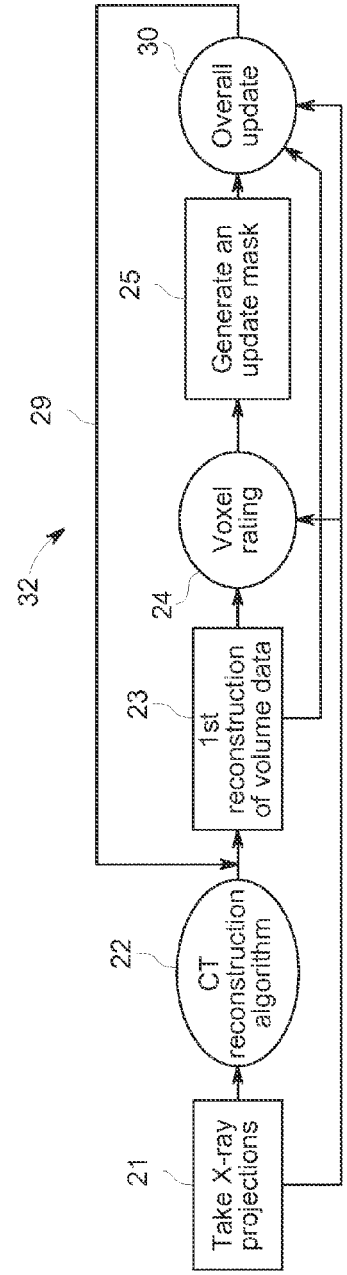
FIG. 2a is a flow diagram illustrating a computed tomography method according to an embodiment of the present invention.

In the computed tomography methods shown in FIGS. 2, 2a the set of x-ray projections 21 taken from the sample 13 with the x-ray system 10 are input to a first, or initial, computed tomography reconstruction algorithm 22. The first reconstruction algorithm 22 is adapted to compute first reconstructed volume data 23 of the sample 13. In the reconstructed volume data 23, the value of each voxel or volume element represents the attenuation coefficient or density in the corresponding volume element of the sample 13. In the present context, the term voxel corresponds to a 3-dimensional pixel and, as usual in the art, denotes the smallest volume element unit to which a single x-ray attenuation coefficient value is assigned. The complete volume data 23 of a sample 13 is given by a set of subsequent volume slices through the whole sample 13. The first reconstruction algorithm 22 is known per se and may be based on any suitable mathematical method, including but not limited to analytical methods like for example Feldkamp or helical reconstruction, iterative methods like algebraic methods, for example ART, SART, etc., or statistical methods like maximum likelihood, etc.

Following the first reconstruction step 22, an iterative reconstruction process 32 is carried out which will be described in the following.

Based on the first reconstructed volume data 23 and the x-ray projections 21 of the sample 13 under inspection, a confidence measure determination process according to EP application 09 01 4798.4 is carried out, which is not shown in FIGS. 2, 2a. This may be done in the computing device 41 or alternatively in an independent computing device. In an embodiment, a forward projection is applied to the reconstructed volume slices 23 for generating artificial projections of the sample 13. The forward projection is a mathematical method which simulates the x-ray system 10 shown in FIG. 1 using geometric projection models of a scanner, taking into account the geometry of the x-ray system 10 shown in FIG. 1 in order to make the artificial projections comparable to the x-ray projections 21 recorded with the x-ray system 10. The artificial projections are one- or two-dimensional artificially computed images each consisting of a plurality of pixels. Based on a comparison between the artificial projections and the x-ray projections 21 recorded with the x-ray system 10, individual confidence measures, or quality measures, for each voxel of the reconstructed volume data 23 are then calculated in a confidence measure calculating step. In more detail, the confidence measure of a voxel may be calculated as follows. For each x-ray projection value of the set of real projections 21, which is influenced by the voxel under inspection, the difference between this projection value and the corresponding artificial projection value is calculated. The confidence measure of the voxel under inspection may then calculated from said differences for all x-rays passing the voxel under inspection, in particular as a sum of these. In this case, if the (absolute) value of the sum is high, the confidence of the voxel under inspection is low, and vice versa. The entity of confidence measures over all voxels results in a confidence measure distribution for all volume slices, i.e. the complete volume, of the sample 13. Other methods for calculating the confidence measure from the differences between real and artificial projections are possible.

In a voxel rating step 24 an evaluation is carried out for each single voxel in the volume slices 23 whether or not this voxel fulfils a predetermined condition indicating that a further update is required for this voxel. This evaluation is based on the voxel confidence measure, or voxel quality measure, of the voxel under inspection. In particular, if the confidence measure of a particular voxel exceeds a predetermined threshold indicating that the quality is sufficient (good voxel), it is determined that an update of this voxel is not required. On the other hand, if the confidence measure of a particular voxel falls below a predetermined threshold indicating that the quality is poor (poor voxel), it is determined that an update of this voxel is required.

From the information regarding all voxels acquired in the voxel rating step 24 an update mask 25 is generated and stored in the memory 44 for further use. The update mask contains the description of those volume parts in terms of single voxels which require an update in a next reconstruction iteration, i.e., the poor voxels. The update mask can for example be a data object containing a one-bit information for every voxel of the reconstructed volume indicating whether or not each voxel requires an update. However, the update mask is not limited to this specific form. It can for example also be a data object containing position information for all poor voxels which require an update, or any other kind of suited data object.

The iterative CT reconstruction process 32 of FIGS. 2, 2a furthermore comprises a reconstruction step 26 of computing update values 27 for single voxels of the volume slices 23 in order to improve their image quality or, more generally, their data quality. The reconstruction step 26 may be based on any suited iterative reconstruction algorithm, in particular algebraic methods like for example ART, SART, etc. Typically, a set of artificial projections is calculated from the volume slices 23, and then from the artificial projections and from the real projections 21 the update values 27 for the voxels are computed.

Figure 3:
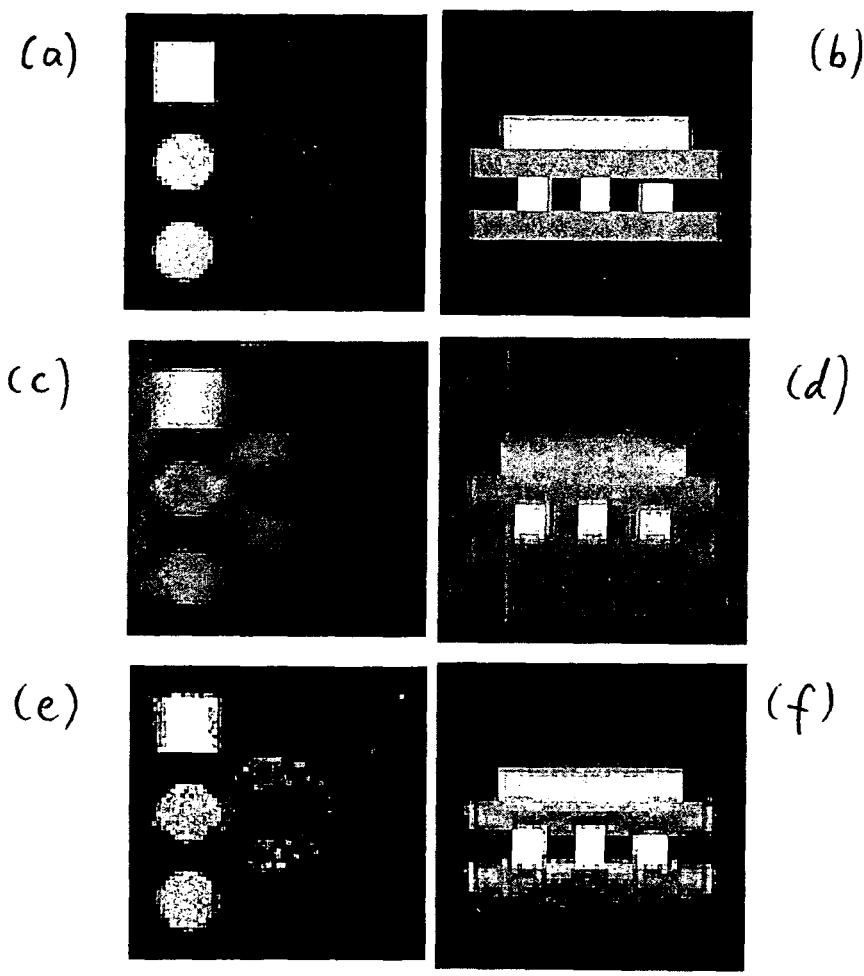
FIGS. 3a, 3b, 3c, 3d, 3e and 3f show example images of volumes slices for two samples (original, reconstructed according to a conventional CT method, and reconstructed according to a CT method according to an embodiment of the present invention).

According to an embodiment of the present invention, the update mask 25 is taken into account in the reconstruction 26, as indicated by the dashed arrow 31 in FIG. 2. Specifically, update values 27 are calculated in the reconstruction step 26 only for the poor voxels as defined by the update mask 25. By disregarding the good voxels in the reconstruction 26, corresponding waste of processing time can be avoided and overall the reconstruction and updating time can be significantly reduced. On the other hand, by defining the volume to be updated on a single voxel level, it can be guaranteed that every single poor voxel is subject to updating in order to improve its quality, which results in an overall improved data quality. This is demonstrated by FIG. 3 showing images (a), (b) of original volume slices of two samples as well as images (c), (d) of volume slices 23 reconstructed by a conventional method without steps 24 and 28 in FIG. 2, and images (e), (f) of volume slices 23 reconstructed by the method according to embodiments of the present invention as shown in FIG. 2 or FIG. 2a. Both in the conventional method and the method according to embodiments of the present invention, the reconstruction has been done from projection data 21 collected from a less than 360°, here for example 106°, rotation of the sample 13. It is clearly evident from a comparison of images (c) and (e), as well as images (d) and (f), that in particular the boundaries of the objects in images (e) and (f) are much clearer as a result of the CT method according to embodiments of the present invention.

On the basis of the update values 27, the values of the volume slices 23 are updated in a reconstructed volume update step 28, but not necessarily only with respect to the poor voxels as defined in the current update mask 25. In this manner, a next-iteration full set of volume slices 23 is generated, as indicated by arrow 29 in FIGS. 2, 2a which completes the iterative reconstruction loop 32. If a not-shown evaluation step determines that a general termination condition is not fulfilled, for example if the overall quality of the current set of volume data 23 may be significantly improved by a further iteration, a next reconstruction iteration step 26 is carried out for further updating the poor voxels.

According to an embodiment of the present invention, the calculation of the single-voxel confidence measures, the voxel rating step 24 and the calculation of the update mask 25 is also carried out iteratively, namely prior to each reconstruction iteration step 26 and on the basis of each updated volume data 23 generated after each reconstruction iteration step 26. In this manner, the volume portion to be updated can be reduced step by step from one iteration 26 to the next iteration 26, and the overall reconstruction and update time can be reduced significantly further.

In the embodiments described with reference to FIGS. 2 and 2a, single-voxel confidence measures calculated only from the projections 21 and the reconstructed volume data 23 are used as a separation criterion for separating the voxels into good and poor voxels. However, the present invention is not limited to using confidence measures calculated only from the CT process data 21, 23. Alternatively, the voxel rating 24 can be based on any kind of predetermined knowledge about the quality of the volume data 23, for example by comparing the reconstructed volume data 23 to pre-stored ideal volume data of an ideal sample taken from a data base.

In the embodiment described with reference to FIG. 2, after each reconstruction step 22, 26 the complete update mask 25 is calculated and only then the update values 27 are calculated in the reconstruction step 26. However, this is not necessarily the case. In an embodiment, for example, for every single voxel, after performing the voxel rating 24, an update value may be calculated for this voxel immediately afterwards if the voxel rating has determined a poor voxel.

Instead of calculating, in step 26, update values only for the poor voxels as defined by the update mask 25, it is also possible to disregard the update mask 25 in step 26 and calculate the update values for all voxels of the complete sample volume. This embodiment corresponds to FIG. 2 with dashed arrow 31 removed. In this embodiment, the update mask 25 is only taken into account in the volume update step 28.

The embodiment shown in FIG. 2a illustrates that steps 26 to 28 of FIG. 2 may be performed in an overall update step 30. In other words, the step of calculating the update values is performed together with the step of updating the volume data in an overall update step 30.

The CT method according to embodiments of the present invention and illustrated in FIGS. 2, 2a may be used in an automated defect recognition (ADR) system for non-destructive testing of industrial products, where an ADR algorithm is applied to the reconstructed volume data in order to determine defects in the sample under inspection. The ADR system may be realized by an ADR software in the computer apparatus 40.

What is claimed is:
1. A computed tomography method for determining a volumetric representation of a sample, comprising:
reconstructing initial volume data of the sample from x-ray projections of the sample taken by an x-ray system;
determining a part of the reconstructed initial volume data to be updated; and executing an iterative update process configured to generate, using an iterative re-construction method, updated volume data only for the part of the reconstructed initial volume data determined to be updated, wherein determining the part of the reconstructed initial volume data to be updated comprises individually evaluating every single voxel in the reconstructed initial volume data, based on available quality information for the reconstructed initial volume data, whether or not the voxel fulfils a predetermined condition indicating that an update is required for the voxel, wherein the iterative update process generates updated volume data only for the voxels which have been determined that an update is required, and wherein the method further comprises determining, from process data of initial reconstructing of initial volume data of the sample and/or calculating update values, individual confidence measures for every single voxel of the reconstructed initial volume data.

2. The method according to claim 1, wherein individually evaluating every single voxel in the reconstructed initial volume data performed in each iteration of the iterative update process.

3. The method according claim 1, wherein individually evaluating every single voxel in the reconstructed initial volume data comprises generating an update mask comprising information about the voxels which have been determined that a further update is required.

4. The method according claim 1, wherein the iterative up-date process only generates the updated volume data for the voxels which the voxel quality falls below, or rises above, a predetermined threshold.

5. The method according to claim 1, wherein the iterative update process comprises calculating update values of the reconstructed initial volume data or directly updating the reconstructed initial volume data by an iterative reconstruction method.

6. The method according to claim 5, wherein calculating update values or directly updating the reconstructed initial volume data is performed only for the voxels which have been determined that an update is required.

7. The method according to claim 5, wherein the iterative update process comprises updating the reconstructed initial volume data using the calculated update values.

8. The method according to claim 7, wherein updating the reconstructed initial volume data is performed only for the voxels which have been determined that an update is required.

9. The method according to claim 1, wherein for a particular voxel under evaluation, individually evaluating every single voxel in the reconstructed initial volume data is further based on the determined individual confidence measure of the voxel being evaluated.

10. The method according to claim 1, wherein the confidence measures are determined on the basis of the reconstructed initial volume data and/or the x-ray projections.

11. The method according to claim 1, wherein determining individual confidence measures is repeated in each iteration of the iterative update process.

12. A computed tomography system, comprising an x-ray system configured to take a set of x-ray projections of a sample, and a computing device configured to:

reconstruct initial volume data of the sample from x-ray projections of the sample taken by an x-ray system;

determine a part of the reconstructed initial volume data to be updated; and execute an iterative update process configured to generate, using an iterative re-construction method, updated volume data only for the part of the reconstructed initial volume data, determined to be updated, wherein determine the part of the reconstructed initial volume data to be updated comprises individually evaluating every single voxel in the reconstructed initial volume data, based on availability quality information for the reconstructed initial volume data, whether or not the voxel fulfills a predetermined condition indicating that an update is required for the voxel, and wherein the iterative update process generates updated volume data only for the voxels which have been determined that an update is required, wherein the iterative update process comprises calculating update values of the reconstructed initial volume data or directly updating the reconstructed initial volume data by an iterative reconstructive method, wherein the computing device is further configured to determine, from process data of initial reconstructing of initial volume data of the sample and/or calculating update values, individual confidence measures for every single voxel of the reconstructed initial volume data, and wherein the confidence measures are determined on the basis of the reconstructed initial volume data and/or the x-ray projections.

* * * * *